United States Patent [19]

Tjia et al.

[11] Patent Number: 5,520,923
[45] Date of Patent: May 28, 1996

[54] FORMULATIONS FOR DELIVERY OF OSTEOGENIC PROTEINS

[75] Inventors: Jane S. Tjia, Malden; Brian D. Kelley, Medford; Richard P. Northey, Ipswich; C. Michael Philbrook, Boston, all of Mass.

[73] Assignee: Genetics Institute, Inc., Cambridge, Mass.

[21] Appl. No.: 308,787

[22] Filed: Sep. 19, 1994

[51] Int. Cl.⁶ .................................. A61F 2/00; A61F 2/28
[52] U.S. Cl. ......................... 424/426; 528/495; 264/321; 623/16
[58] Field of Search ..................... 424/486, 484, 424/426; 623/16; 528/495; 264/321

[56] References Cited

U.S. PATENT DOCUMENTS

| | | | |
|---|---|---|---|
| 4,164,794 | 8/1979 | Spector et al. | 623/16 |
| 4,186,448 | 2/1980 | Brekke et al. | |
| 4,394,370 | 7/1983 | Jeffries et al. | |
| 4,455,256 | 6/1984 | Urist. | |
| 4,526,909 | 7/1985 | Urist. | |
| 4,563,489 | 1/1986 | Urist | 524/21 |
| 4,645,503 | 2/1987 | Yamazaki. | |
| 4,652,441 | 3/1987 | Okada et al. | |
| 4,711,782 | 12/1987 | Okada et al. | |
| 4,877,864 | 10/1989 | Wang et al. | |
| 4,917,893 | 4/1990 | Okada et al. | |
| 4,954,298 | 9/1990 | Yamamoto et al. | |
| 5,001,691 | 5/1961 | Oppermann et al. | |
| 5,013,649 | 5/1991 | Wang et al. | |
| 5,061,492 | 10/1991 | Okada et al. | |
| 5,108,753 | 4/1992 | Kuberasampath. | |
| 5,133,755 | 7/1992 | Brekke | 623/16 |
| 5,171,579 | 12/1992 | Ron et al. | 424/486 |
| 5,266,683 | 11/1993 | Oppermann et al. | 530/326 |
| 5,366,508 | 11/1994 | Brekke et al. | |

FOREIGN PATENT DOCUMENTS

| | | |
|---|---|---|
| 154434 | 2/1985 | European Pat. Off. . |
| WO93/06872 | 4/1993 | WIPO . |

OTHER PUBLICATIONS

Lyons et al., Proc. Nat'l. Acad. Sci. USA 86:4554–4558 (1989).
Yamazaki et al. Clin. Orthop. and Related Research 234:240–249 (1988).

*Primary Examiner*—Peter F. Kulkosky
*Attorney, Agent, or Firm*—Steven R. Lazar; Thomas J. DesRosier

[57] ABSTRACT

A formulation is disclosed comprising a pharmaceutically acceptable admixture of an osteogenic protein and a sponge of porous particulate polymer matrix. The sponge may be prepared by treating the porous particulate polymer matrix with a suitable fusing material such as ethanol and a surfactant such as a polysorbate.

12 Claims, No Drawings

FORMULATIONS FOR DELIVERY OF OSTEOGENIC PROTEINS

BACKGROUND OF THE INVENTION

The subject invention relates to the field of osteogenic proteins and pharmaceutical formulations thereof. More particularly, the subject invention involves pharmaceutical formulations designed to sequester osteogenic protein in situ and to provide a bioresorbable scaffolding for a time sufficient to allow the protein to induce cartilage and/or bone formation through differentiation of uncommitted mesenchymal cells into osteoblasts.

Osteogenic proteins are those proteins capable of inducing, or assisting in the induction of, cartilage and/or bone formation. Many such osteogenic proteins have in recent years been isolated and characterized, and some have been produced by recombinant methods. For example, so-called bone morphogenic proteins (BMP) have been isolated from demineralized bone tissue (see e.g. Urist U.S. Pat. No. 4,455,256); a number of such BMP proteins have been produced by recombinant techniques (see e.g. Wang et al. U.S. Pat. Nos. 4,877,864 and Wang et at. 5,013,549); a family of transforming growth factors TGF-α and TGF-β) has been identified as potentially useful in the treatment of bone disease (see e.g. Derynck et at., EP 154,434); a protein designated Vgr-1 has been found to be expressed at high levels in osteogenic cells (see Lyons et al. (1989) Proc. Nat'l. Acad. Sci. USA 86, 4554–4558); and proteins designated OP-1, COP-5 and COP-7 have purportedly shown bone inductive activity (see Oppermann, et at. U.S. Pat. No. 5,001,691).

Various attempts have been made at developing formulations designed to deliver osteogenic proteins to a site where induction of bone formation is desired. For example, certain polymeric matrices such as acrylic ester polymer (Urist, U.S. Pat. No. 4,526,909) and lactic acid polymer (Urist, U.S. Pat. No. 4,563,489) have been utilized, but these formulations do not sequester the osteogenic protein for a time sufficient to optimally induce bone formation, and further have been found to erode too slowly for optimal bone formation.

A biodegradable matrix of porous particles for delivery of an osteogenic protein designated as OP is disclosed in Kuberasampath, U.S. Pat. No. 5,108,753. While U.S. Pat. No. 5,108,753 discloses that a successful carder for OP must bind the protein, act as a slow release delivery system, accommodate each step of the cellular response during bone development, and protect the protein from nonspecific proteolysis, no formulations are suggested which contain components that specifically sequester the OP at the site where bone formation is desired.

Ron et al., U.S. Pat. No. 5,171,579 discloses that the average surface area per porous particle is critical to optimize bone formation.

Brekke et al., U.S. Pat. Nos. 4,186,448 and 5,133,755 describe methods of forming highly porous biodegradable materials composed of polymers of lactic acid COPLA).

Okada et al., U.S. Pat. Nos. 4,652,441, 4,711,782, 4,917, 893 and 5,061,492 and Yamamoto et al., 4,954,298 disclose a prolonged-release microcapsule comprising a polypeptide drug and a drug-retaining substance encapsulated in an inner aqueous layer surrounded by a polymer wall substance in an outer oil layer.

Yamazaki et al., Clin, Orthop. and Related Research, 234:240–249 (1988) disclose the use of implants comprising 1 mg of bone morphogenetic protein purified from bone and 5 mg of Plaster of Parris. U.S. Pat. No. 4,645,503 discloses composites of hydroxyapatite and Plaster of Paris as bone implant materials.

Collagen matrices have also been used as delivery vehicles for osteogenic proteins (see e.g. Jeffries, U.S. Pat. No. 4,394,370), but collagen frequently causes undesirable antigenic reactions in patients. Therefore, there remains a need for a pharmaceutical formulation capable of sequestering osteogenic proteins at a site where induction of bone formation is desired for a time sufficient to allow safe, effective induction of such bone formation.

SUMMARY OF THE INVENTION

In U.S. Pat. No. 5,171,579, it is disclosed that osteogenic proteins can be sequestered at a site where bone inducing activity is desired using autogenous blood, without using antifibrinolytic agents, provided that a porous particulate polymer matrix is incorporated into the formulation. To reduce the preparation time and improve the above formulation's handling characteristics, Applicants have found that it is desirable to fabricate the porous particulate polymer matrix into the form of a fused sponge, which is preferably wettable and slightly malleable. The fused sponge may be made by wetting the porous particulate polymer matrix with a suitable liquid fusing composition. A preferred liquid fusing composition is comprised of 95% ethanol and 0.05% polysorbate or other non-ionic surfactant. The liquid composition may be added to the particles, preferably in a ratio of about 0.75 to about 0.85 liquid:particles (v/v).

In one embodiment, the subject invention provides methods for preparing fused sponges useful as a carrier for osteogenic proteins. In another embodiment, the invention comprises compositions comprising a pharmaceutically acceptable admixture of an osteogenic protein together with a fused sponge formed of a porous particulate polymer, the particles of which have been fused into a fused sponge form using appropriate processing. The formulations may optionally include other protein sequestering agents, particularly cellulosic materials.

The methods and compositions of the present invention are useful for the preparation of formulations of osteoinductive proteins which can be used, among other uses, to promote the formation of cartilage and/or bone, for repair of tissue damage and fractures.

The inventors have found that, by heating porous particulate polymeric material, preferably copolymers of lactic acid and glycolic acid (PLGA), to a temperature above its glass transition temperature fig), it is possible to fuse them together. However, heating PLGA particles alone results in co-polymer chain mobility and ultimately to particle collapse. This leads to a very dense, non-porous structure, which is undesirable. The inventors have surprisingly found that this undesirable effect can be overcome by adding a liquid containing a lower alkyl alcohol (i.e., $C_1$–$C_5$), preferably ethanol, and heating the composition in a sealed container. Adding an external plasticizer which is a poor solvent or non-solvent for PLGA in a lower alkyl alcohol, such as ethanol, will lower the Tg of the polymer. If the external plasticizer has a low diffusion coefficient in the polymer, the surfaces of the polymer will fuse together before the particle fully collapses.

DETAILED DESCRIPTION OF THE INVENTION

Accordingly, the present invention comprises processes of preparing fused sponges of porous particulate polymer, which fused sponges are suitable for use as a carrier for osteogenic protein. Generally, the process comprises:

a) preparing a mixture of particles of a porous particulate polymer, a lower alkyl alcohol and a surfactant;

b) heating the mixture of step (a) until the particles form a fused sponge;

c) optionally continuing to heat the mixture for an additional period of time at a temperature of about 45° to 60° C.;

d) optionally cooling the mixture; and e) drying the mixture in the form of a fused sponge.

In a preferred embodiment, the particles are made of co-polymers of lactic acid and glycolic acid.

The porous particulate polymer matrix component useful in the practice of the subject invention is a polymeric material that can be formed into the fused sponges of porous particles as described below thereby providing in situ scaffolding for the osteogenic protein, while having biodegradable properties allowing for replacement by new bone growth. Examples are polymers which may be useful in the present invention include polymers of amino acids, orthoesters, anhydrides, propylene-co-fumarates, or a polymer of one or more α-hydroxy carboxylic acid monomers, (e.g. α-hydroxy acetic acid (glycolic acid) and/or α-hydroxy propionic acid (lactic acid)). The latter can be employed in its d- or l- form, or as a racemic mixture, the racemic mixture being preferred. The preferred polymers for use in preparing the formulations of the present invention are copolymers of lactic acid and glycolic acid (PLGA).

When copolymers of lactic acid and glycolic acid are employed (PLGA), the molar ratio of monomers can range from 1:99 to 99:1 depending upon the desired bioerosion lifetime which in turn depends upon the clinical indication being addressed, as more than 50% of either monomer gives longer bioerosion lifetime (slower biodegradation). The molecular weight of the polymer can range from about 1,000 to 100,000 (relative to polystyrene in $CHCl_3$) with 30,000–50,000 being preferred when a 50:50 copolymer is employed. In general, the higher the molecular weight, the slower the biodegradation.

The polymeric matrix component of the subject invention is used in the form of highly porous to hollow (with surface porosity) particles, hereinafter collectively referred to as "porous particles." These porous particles are generally spherical having diameters of 150 to 850 μm, preferably 150 to 500 μm, most preferably 300 to 500 μm. This particle size creates sufficient spacing between particles to allow mammalian osteoprogenitor cells to infiltrate and be positively influenced by (evidenced by an increase in osteogenic activity/bone growth rate) the osteogenic protein.

U.S. Pat. No. 5,171,579 discloses that the average surface area per porous particle is critical to optimize bone formation. Specifically, porous particles useful in bone formation according to the present invention should have an average surface area of from about 0.02 to 4 $m^2/g$. The disclosure of U.S. Pat. No. 5,171,579 is hereby incorporated herein by reference. WO 93/06872 further discloses that it is possible to produce porous particles having the desired surface area by introducing a "porosigen" (composition capable of imparting porosity by increasing particle surface area) into the solution used to produce the porous particles. The disclosure of WO 93/06872 is hereby incorporated herein by reference. It is also possible to control the bioerosion rate by subjecting the porous particles to sterilizing doses of γ radiation. The higher the γ radiation dose, the faster the bioerosion. Particles useful herewith have a porosity such that the surface area of the particles is increased about 2–250 fold over the surface area of non-porous particles of comparable size.

A preferred method of production of the porous particles useful in the invention is, generally speaking, a solvent evaporation process comprising dissolving the polymer (in e.g. $CH_2Cl_2$), and adding a porosigen such as NaCl, mannitol or sucrose in solid and/or liquid form. When porosigen is added in solid form, the matrix-porosigen solution takes the form of a suspension. Another preferred method of production of the porous particles useful in the invention is a solvent extraction method, wherein the porosigen is added in liquid form with concomitant homogenization. When porosigen is added in liquid form with homogenization, the matrix-porosigen solution takes the form of an emulsion. With either method, the matrix-porosigen emulsion is added to an excess aqueous solution containing surfactant such as poly(vinyl alcohol) with controlled stirring and temperature. The resultant porous particles are hardened by extracting or evaporating residual solvent, and dried. PLGA particles useful in the subject invention made utilizing 50% NaCl as a porosigen have a surface area of between about 0.2 and 0.6 $m^2/g$; and particles made using sucrose as a porosigen have a surface area of between about 0.04 and 0.09 $m^2/g$. PLGA particles useful in the present invention made using liquid porosigen with homogenization have a surface area of between about 0.02 and 4 $m^2/g$.

Other methods of preparing porous particulate polymer for use in the present invention, in which the above steps can be varied and additional steps can be performed are within the skill of the art.

The liquid useful for fusing the porous particulate polymer to form a fused sponge comprises a lower alkyl alcohol, preferably ethanol, and may further comprise a surfactant. The alcohol is preferably in a concentration of from about 50% to about 100% volume/volume, more preferably from about 70% to about 100%. The most preferred concentration of ethanol is about 95%. Substances other than lower alkyl alcohols may also be useful provided that they have a low diffusion coefficient in PLGA, are able to wet the PLGA particles and are able to create vapor pressure to create voids or pores between the particles.

The surfactant useful in the liquid is preferably a nonionic surfactant, such as a polyoxyester, for example polysorbate 80, polysorbate 20 or Pluronic F-68. The most preferred surfactants include Polysorbate 80, commercially available as Tween 80. The surfactant is preferably present in a range from about 0 to about 4% volume/volume, more preferably from about 0.01 to about 0.05%.

Preferably the ratio of total liquid:solid during heating, that is the ratio of ethanol and surfactant to particles, is from about 0.70 to about 0.90 volume/volume. It is most preferred that the liquid:solid ratio be in the range from about 0.75 to about 0.85.

The container useful for heating the particles and liquid is preferably made of polystyrene. Other materials known in the art, such as polypropylene, may also be useful containers for heating the particles. Preferably, the container is sealed. The container is preferably in the shape and size which is desired for the fused sponge, such as rectangular or cylindrical. Alternatively, the fused sponge may be cut to a preferred size or shape after formation of the fused sponge.

The container is used as a mold for the formation of a fused sponge. The liquid and the particles may be added to the container in any order or simultaneously. After being added to the container, the liquid and particles are mixed, stirred or otherwise manipulated to ensure even distribution of the liquid and the particles.

The liquid and particles mixture is heated at a temperature and for a period of time sufficient to form a fused sponge structure, preferably from about 1 to about 60 minutes until the particles and liquid reach a temperature of about 45° to 60° C. The heating may be accomplished using any suitable heating means. Heating is preferably accomplished using a circulating water bath. Fusion may be accomplished at a constant temperature, or using a temperature gradient. If a constant temperature is used, it is preferably about 60° C. and the mixture is preferably heated for a period of time suitable to allow fusion of the particles and liquid into a fused sponge, generally, about 1 to 60 minutes, most preferably about 10 minutes. If a temperature gradient is used, the heating preferably begins at a temperature of about 26° C. to about 40° C. and the temperature increased at an acceptable rate, preferably about 1.7° C./minute, until it reaches about 45° to 60° C., most preferably about 60° C. Once the mixture reaches the desired temperature, the container may be removed immediately from the bath. Optionally, heating of the mixture at a temperature of about 45° to 60° C. may continue for an additional period of time from about 1 to about 60 minutes.

The fused sponge may be removed from the container immediately upon removal of the container from the water bath. Alternatively, the fused sponge may be allowed to cool or may be refrigerated, preferably in a 4° C. water bath, for a period of time, preferably for a time of about 5 minutes or more, before removing the fused sponge from the container. The cooling step aids in preventing collapse of the sponge which can occur with slow cooling at room temperature. If necessary, forceps or similar means may be used to remove the fused sponge from the container. After removal from the container, the fused sponge is allowed to dry.

The osteogenic proteins useful with the fused sponges made in accordance with the subject invention are well known to those skilled in the art and include those discussed above. The preferred osteogenic proteins for use herein are those of the BMP class identified as BMP-1 through BMP-12 in U.S. Pat. Nos. 4,877,864; 5,013,649; WO 90/11366 published Oct. 4, 1990; WO 91/18098 published Nov. 28, 1991; WO 93/00432, published Jan. 7, 1993; U.S. Ser. Nos. 08/247,908 and 08/247,904, both filed May 20, 1994; and U.S. Ser. No. 08/217,780, filed on Mar. 25, 1994. The disclosure of the above publications are hereby incorporated by reference. The most preferred is BMP-2, the full length cDNA sequence of which is described in detail in the '649 patent. Of course, combinations of two or more of such osteogenic proteins may be used, as may fragments of such proteins that also exhibit osteogenic activity. Such osteogenic proteins are known to be homodimeric species, but also exhibit activity as mixed heterodimers. Heterodimeric forms of osteogenic proteins may also be used in the practice of the subject invention. BMP heterodimers are described in WO93/09229, the disclosure of which is hereby incorporated by reference. Recombinant proteins are preferred over naturally occurring isolated proteins. The amount of osteogenic protein useful herein is that amount effective to stimulate increased osteogenic activity of infiltrating progenitor cells, and will depend upon the size and nature of defect being treated as discussed in more detail below, such amounts being orders of magnitude less than the amount of porous particulate polymer matrix employed, generally in the range of 1–50 µg of protein for each 10 mg of fused sponge employed and more preferably in the range of 0.5–10 µg protein for each milligram of fused sponge employed (assuming approximately 0.2 g/cc density).

The osteogenic proteins can be utilized in the form of a pharmaceutically acceptable solution (including reconstitution from a lyophilized form). It is optimal to solubilize the osteogenic protein at concentrations of at least about 1 mg/ml, preferably about 2 to 8 mg/ml, so that a pharmaceutically effective amount of protein can be delivered without undue volumes of carrier being necessary. For some applications, concentrations above 2 mg/ml may be desirable. Amino acids having a net positive charge (e.g. net 1+species such as arginine, histidine, lysine and the ethyl esters of glycine and beta-alanine), preferably a net 2+charge (e.g. the ethyl ester of histidine, the methyl esters of lysine and arginine, and agmatine), are useful in this regard. Amino acids having a net zero charge are useful in this regard provided that the positive charge of the compound is sufficiently distant (at least 2–3 $CH_2$ units away) from the neutralizing negative charge (e.g. net neutral species such as gamma-amino butyric acid, beta-amino propionic acid, and glycine-glycine dipeptide). Other solubilizing agents useful herein include poly(sorbate), dextran sulfate, guanidine, heparin, sodium chloride, glutamic acid hydrochloride, acetic acid and succinic acid. For use in solubilizing dimeric BMP, such as BMP-2, 3, 4, 5, 6, 7, 8, 9 and 10 and heterodimers of BMPs such as BMP-2/6 and BMP-2/7, preferred solubilizing agents include arginine and histidine (including esters thereof) and glutamic acid hydrochloride. A preferred solubilizing agent is glutamic acid hydrochloride (HCl). The above formulations may be lyophilized and reconstituted with water, providing for advantages in storage, shipping and stability. A preferred formulation of osteogenic protein at 4.0 mg/ml comprises the following components listed in Table 1:

TABLE 1

| osteogenic protein buffer solution: | 4.0 mg/ml (11.42% wt) |
|---|---|
| glutamic acid HCl | 0.918 mg/ml (2.62% wt) |
| glycine | 25 mg/ml (71.39% wt) |
| sucrose | 5 mg/ml (14.28% wt) |
| polysorbate 80 | 0.1 mg/ml (0.29% wt) |

The porous nature of the particles useful in the present invention creates sufficient surface area for protein adsorption and increases biodegradation, the desirable extent of both being dependent upon the clinical indication being addressed. Surface area can be measured by any conventional technique. For example, BET surface area analysis can be employed using a Micromeritics ASAP 2000 system, which measures surface area based upon adsorption and desorption of Krypton gas at the surface and within the pores of the solid sample. The unit calculates and prints out the surface area:

$$\frac{1}{VA[(P_0/P)-1]} = \frac{C-1}{V_mC}(P/P_0) + \frac{1}{V_mC}$$

$V$ = volume absorb at pressure $P$   $P_0$ = saturation pressure
$P/P_0$ = relative pressure   $P$ = pressure
$C$ = constant   $A$ = gas cross sectional
$Vm$ = Monolayer Capacity   area By plotting $$\frac{1}{VA((P_0/P)-1}\ \text{vs}\ P/P_0,$$

the slope being $$\frac{C-1}{V_mC}$$

and the intercept being $$\frac{1}{V_mC},$$

the surface area $$S_t = \frac{V_m NA}{V}$$

where N=Avogadro's number and V=molar volume.

The amount of sponge used to treat a particular defect will, of course, depend upon the size of the defect being treated, and on the effective amount required to adsorb the osteogenic protein.

Additional optional components useful in the practice of the subject application include, e.g. cryogenic protectors such as mannitol, sucrose, lactose, glucose, or glycine (to protect the formulation from degradation during lyophilization), antimicrobial preservatives such as methyl and propyl parabens and benzyl alcohol, antioxidants such as EDTA, citrate, and BHT (butylated hydroxytoluene), and surfactants such as poly(sorbates) and poly(oxyethylenes), etc. Of course, the traditional preparation of formulations in pharmaceutically acceptable form (i.e. pyrogen free, appropriate pH and isotonicity, sterility, etc.) is well within the skill in the art and is applicable to the formulations of the subject invention.

In certain uses, the formulations of the subject invention may be used in combination with various bone cements, including erodible bone cements such as poly(propylene-co-fumarate) and certain hydroxyapatite cements. Also, certain of these uses will utilize bioerodible hardware such as erodible plates, screws, etc. The dosage regimen will be determined by the clinical indication being addressed, as well as by various patient variables (e.g. weight, age, sex) and clinical presentation (e.g. extent of injury, site of injury, etc.). In general, the dosage of osteogenic protein will be in the range of from about 10 to 1000 μg, preferably from about 10 to 100 μg per 100 μL sponge volume.

The osteogenic protein and fused sponges of porous particulate polymers of the formulations may be provided to the clinic as a single formulation, or the formulation may be provided as a multicomponent kit wherein, e.g. the osteogenic protein is provided in one vial and the porous particulate polymeric fused sponge is provided separately.

The formulations of the subject invention provide malleable implants that allow therapeutically effective amounts of osteoinductive protein to be delivered to an injury site where cartilage and/or bone formation is desired. Such an implant may be used as a substitute for autologous bone graft in fresh and non-union fractures, spinal fusions, and bone defect repair in the orthopaedic field; in cranio/maxillofacial reconstructions; for prosthesis integration, especially as a surface coating to improve fixation of prosthetic implants such as hydroxyapatite coated prostheses; in osteomyelitis for bone regeneration; and in the dental field for augmentation of the alveolar ridge and periodontal defects and tooth extraction sockets. When used to treat osteomyelitis or for bone repair with minimal infection, the osteogenic protein may be used in combination with porous microparticles and antibiotics, with the addition of protein sequestering agents such as alginate, cellulosics, especially carboxymethylcellulose, diluted using aqueous glycerol.

The antibiotic is selected for its ability to decrease infection while having minimal adverse effects on bone formation. Preferred antibiotics for use in the devices of the present invention include vancomycin and gentamycin. The antibiotic may be in any pharmaceutically acceptable form, such as vancomycin HCl or gentamycin sulfate. The antibiotic is preferably present in a concentration of from about 0.1 mg/mL to about 10.0 mg/mL.]

The following examples are illustrative of the present invention and are not limiting in any manner. Modifications, variations and minor enhancements are contemplated and are within the present invention.

EXAMPLE 1

Preparation of Porous Particulate Polymeric Matrix

Porous particles of PLGA are produced in accordance with the methods described in International Patent Application WO 93/00050, and U.S. Pat. No. 5,171,579, the disclosure of which is hereby incorporated by reference herein.

EXAMPLE 2

Preparation of Sponges of Porous Particulate Polymeric Matrix

A. Sponge Integrity and Wettability

PLGA particles of diameter of approximately 300 to 500 μm are placed in a 1.5 ml Eppendorf vial [internal diameter=8 mm, length=43 mm] with screw caps. 95% ethanol, or 95% ethanol and 0.05% Tween 80 (polysorbate 80) surfactant, is then added and the PLGA particles are packed as tightly as possible by tapping the vial against a hard surface. The vials are capped and immersed in a circulated water bath at 45° C. for 10 minutes. The vials are then removed and decanted. The fused sponge formed is removed from the tube and allowed to air dry overnight. The resulting cylinder is 7 mm in diameter and approximately 40 mm in length. The fused sponge is sectioned into pieces 5 mm in length [approximately 200 μl] and tested for wettability with water and the buffer solution shown in Table 1 above. Rectangular fused sponges are also made using disposable cuvettes as molds. The cuvettes are sealed with two layers of aluminum foil and parafilm. Additional fused sponges are made with 95% ethanol and 0.05% Tween 80 surfactant using 1.5 ml Eppendorf tubes.

Structural Integrity: The fused sponges show a surprisingly high resistance to tensile forces and maintain their shape under high strain. Fused sponges made without any additives have the highest structural integrity. They show a relatively high degree of resistance to tension. Rectangular fused sponges have a higher resistance than cylindrical fused sponges.

Wettability: After being allowed to dry for approximately 24 hours, both the fused sponges with ethanol and those made with ethanol and surfactant wicked quickly and easily. Over time, the fused sponges made with only ethanol gradually lose their quick wicking ability. Those made with surfactant retain their wickability. The cylindrical sponges wick water slightly better than the rectangular sponges. Newly formed cylindrical sponges, both with and without added surfactant, are able to wick approximately ⅔ of their volume per ml of sponge.

B. Process Parameter Optimization:

PLGA particles of diameter of approximately 300 to 500 μm are placed in a suitable container and wetted with 95% ethanol, 0.5% Tween 80 surfactant in a ratio of 0.75 (v/v) ethanol/PLGA particles to form a slurry. The resulting slurry is stirred to ensure even distribution of the particles throughout the ethanol and to remove any large air bubbles which may exist. The mold is sealed and the sponge is heated in a circulating water bath. After heating, the mold is unsealed and allowed to cool before the fused sponge is removed from the mold and allowed to dry. Removal is accomplished by inverting the mold, and depending upon the mold material, either lightly shaking or vigorously tapping the mold against a hard surface until the fused sponge is loosened.

Effect of Temperature:

Fused sponges were made at water bath temperatures ranging from 30 to 75° C. Temperatures are selected to exceed glass transition temperatures of the PLGA particles to ensure that some fusion would take place at the lowest temperature (30° C.). Higher temperatures were examined to see how porosity is affected by more extreme conditions.

Fusion at a constant temperature as well as with a temperature gradient was studied. Two starting temperatures were used for the temperature gradients: 26.4° C. and 40.0° C. Once the molds were placed in the water bath, the temperature was set for 60.0° C. and the water bath was allowed to heat up at an average rate of 1.7° C./min. Once the water bath reached 60°, the fused sponges were either removed immediately or held for 5 minutes before removal. The temperature inside and outside the mold was monitored using a thermocouple in order to better understand sponge and pore formation.

In general, friability decreased as fusion temperature increased. However, deformation of both the PLGA particles and the fused sponge itself was more prevalent as fusion temperature increased. At a temperature of 60° C., sufficient fusion is achieved without completely melting the PLGA particles and with minimum friability. At temperatures greater than 60° C., the PLGA particles lose their structure and overfusion occurs. All of the fused sponges made using a temperature gradient have good porosity. Those removed from the water bath immediately after it reached 60° C. also have excellent sponge shape. The fused sponges held for 5 minutes at 60° C. were noticeably more difficult to remove from the mold. Forceps had to be used to facilitate removal, resulting in deformation of the fused sponge.

Regardless of whether a temperature gradient was used, the inside of the mold approaches the temperature of the surrounding water bath within 2.5 minutes. When 26° C. is the initial temperature, the temperature inside the mold is always slightly below that of the water bath. Acceptable fused sponges are formed using both of these methods.

Effect of Time:

Sponges were heated from 1 to 60 minutes at 60° C. After 1 minute, fusion has already occurred. However, at 1 and 2 minutes, the sponges are prone to a noticeable amount of shedding of particles from the edges when the fused sponge is handled. Friability and shedding noticeably decreases as time is increased. After 1 hour, shedding and friability are minimal. Porosity increases with heating up to 10 minutes. After 10 minutes, further heating only serves to decrease friability.

Removal of fused sponges from the molds becomes increasingly difficult as time increases. At 10 and 15 minutes, a spatula was needed to facilitate removal. However, this does not appear to have a negative effect on the dimensions of the fused sponge when compared to those that did not require the use of a spatula.

Density of the fused sponges was measured at 0,5,10 and 15 minutes. The time of heating has little effect on density. The average density of the fused sponges is 0.17 g/cc.

Effect of Ethanol/Surfactant:PLGA Ratio:

A mixture of ethanol and surfactant, such as Tween 80, is added to the PLGA particles to act as an external plasticizer and to lower the glass transition temperature (Tg). To determine an optimal ratio of ethanol/surfactant:PLGA particles, ethanol/Tween was added to PLGA particles in volume-to-volume ratios ranging from 0.60 to 0.90.

At low ratios (<0.70), sponge deformation tended to occur. This may be due to the possibility that not all of the particles are adequately covered with ethanol. Thus, some particles may have undergone bulk chain mobility and collapse. At ratios of 0.9 or higher, the resulting fused sponges tend to be soft and friable. The greater the amount of ethanol present, the greater the total volume of the slurry and the greater the average distance between particles in the slurry. Thus, at high ethanol volumes, there is less particle-to-particle contact resulting in less, and weaker points of fusion. The liquid to solid (ethanol/surfactant:PLGA) ratio should therefore be in the range of about 0.70 to about 0.90. At a ratio of 0.75, the fused sponge is harder and more rigid than that made at 0.9 and maintains the shape better than at 0.70. Thus, preferred liquid to solid ratios are in the range of about 0.75 to about 0.85.

Effect of Ethanol Concentration:

Sponges were made at 60° C. for 1 hour with ethanol concentrations ranging from 50 to 100% in water. It was found that porosity decreases and sponge deformation increases with decreasing ethanol concentration. However, no appreciable differences in the overall structural integrity existed among the fused sponges.

Effect of Particle Size:

Upon addition of ethanol to the PLGA particles in the mold, a particle density gradient was observed with those particles less than 500 μm. More particles were present at the bottom of the mold than at the top. The gradient was visually less severe as particle size increased. In order to better distribute the particles, molds were tapped for a longer period of time. No density gradient was observed with particles greater than 500 μm in size.

All fused sponges made with particles less than 500 μm were similar in final appearance. Slight porosity gradients were observed with those fused sponges made from 150-250 tμm particles. This is most likely a direct result of the particle density gradient. However, all of these fused sponges (<500 μm) had good porosity, shape and structural integrity.

Fused sponges made with 500–710 μparticles were noticeably less rigid and more friable than those made with smaller particles. These sponges were easily broken when removed from the mold and had slightly greater porosity than the other fused sponges. Because these particles are bigger, there is less contact between particles which could account for the decrease in structural integrity. These fused sponges were also more difficult to remove from the molds intact because of the large pores present. When dry, it was noticed that there was a significant amount of shedding of the particles from the fused sponge when it was handled. This was not the case with fused sponges made from particles less than 500 μm.

Effect of Mold Material:

Fused sponges made with polystyrene as a mold typically contain interparticle pores greater than 300 μm, but contain relatively few pores which are in the range 40–300 μm. Fused sponges made using polypropylene tend to have more interparticle pores in the range 40–300 μm. Because PLGA particles are porous, all fused sponges have intraparticle pores less than 40 μm. Fused sponges made with polypropylene tended to have higher density than those made with polystyrene. For this reason, polystyrene is the preferred mold material, although both polypropylene and teflon may be acceptable.

Removal of the fused sponges from polypropylene and teflon is easier than from polystyrene. Removal from a stainless steel mold was very difficult.

EXAMPLE 3

Rat Ectopic Study

Long-Evans male rats were divided into test groups of five rats each. Each received a subcutaneous implant, 200 μL in size, with a PLGA sponge fused at 60° C. for 60 minutes with rhBMP-2 doses of 0, 10, 20 and 40 μg/100 μL implant. Two alternate formulations of PLGA sponges were prepared which varied the extent of PLGA fusion (underfused=60° C. for 10 minutes; overfused=65° C. for 10 minutes) which were tested at rhBMP-2 doses 10 and 40 μg/100 μL implant to determine of extent of fusion effects the efficacy of the device. After 14 days, the rats were sacrificed and each animal was evaluated for bone formation. As a control, implants comprised of unfused porous PLGA particles in an autologous blood clot matrix, as described in U.S. Pat. No. 5,171,579. The control implants contained 10 μg rhBMP-2/100 μL implant.

The results of the rat ectopic study are summarized in Table 2. The fused sponges of PLGA particles achieved average bone scores between 1.0 and 2.0. No significant differences were found between underfused and overfused devices in either of the doses (10, 40 μg/100 μl rhBMP-2) evaluated. This suggests that the loss of microporosity resulting from overfusion of PLGA does not significantly impact bone formation in this model. All rhBMP-2 containing devices showed evidence of some bone growth on both the periphery and the interior of the implant, although homogeneity of interior bone growth varied among groups.

TABLE 2

| Test Group | Cartilage | Bone | BEP/Matrix Residual Score | Implant Wet Weight (Grams) |
|---|---|---|---|---|
| Control/10 | 0.1 | 0.85 ± 0.47 | 1.6 | 0.597 ± 0.268 |
| PLGA/A/0 | 0 | 0 | 2.4 | 0.081 ± 0.051 |
| PLGA/A/10 | 0.2 | 1.05 ± 1.07 | 2.6 | 0.122 ± 0.049 |
| PLGA/A/20 | 0.15 | 1.35 ± 0.85 | 2.3 | 0.259 ± 0.179 |
| PLGA/A/40 | 0.05 | 1.7 ± 0.82 | 2.6 | 0.174 ± 0.072 |
| PLGA/B/10 | 0.2 | 1.25 ± 0.92 | 2.2 | 0.129 ± 0.050 |
| PLGA/B/40 | 0.15 | 2.1 ± 0.88 | 2.4 | 0.269 ± 0.141 |
| PLGA/C/10 | 0.1 | 1.3 ± 0.92 | 2.4 | 0.220 ± 0.167 |
| PLGA/C/40 | 0 | 2.0 ± 0.67 | 2.6 | 0.272 ± 0.183 |

Control = Unfused PLGA particles in blood clot matrix
PLGA/A = Particles fused at 60° C. for 60 minutes
PLGA/B = Particles fused at 60° C. for 10 minutes ("underfused")
PLGA/C = Particels fused at 65° C. for 10 minutes ("overfused")
Bone and Cartilage scores: Samples were scored on a scale of 0–5 for presence of new bone as per the following table: 5 = 80–100% of the section; 4 = 60–80% of the section; 3 = 40–60% of the section; 2 = 20–40% of the section; 1 = 10–20% of the section; 0.5 = <10% of the section (not significant); 0 = not observed in the section
Residual Bioerodible Particles (BEP) or residual matrix within implants were scored on a scale of none (0), low (1), medium (3) or high (5) for the presence of residual BEP in the implant.

We claim:

1. A method or making a fused bioresorbable sponge suitable for use as a carrier for osteogenic protein, said method comprising:

a) preparing a mixture of particles of a porous particulate polymer made of a material selected from the group comprised of polylactic acid, polyglycolic acid, and copolymers of lactic acid and glycolic acid, and liquid comprising a lower alkyl alcohol and a surfactant, such that the ratio of liquid to particles in the mixture is from about 0.70 to about 0.90 (volume/volume);

b) heating the mixture of step (a) until the particles form a fused sponge;

c) optionally continuing to heat the mixture for an additional period of time at a temperature of about 45° to 60° C.;

d) optionally cooling the mixture; and e) drying the mixture in the form of a fused bioresorbable sponge.

2. The method of claim 1, wherein the porous particulate polymer comprises copolymers of lactic acid and glycolic acid.

3. The method of claim 1 wherein step (b) comprises immersing the particles and liquid in a circulating water bath.

4. The method of claim 3, wherein the starting temperature of the circulating water bath is about 26° C.

5. The method of claim 3, wherein the starting temperature of the circulating water bath is about 40° C.

6. The method of claim 1 wherein the container is made of polystyrene.

7. The method of claim 1 wherein the particles have an average size of approximately 150 to about 500 μm.

8. The method of claim 1 wherein the particles have an average size of approximately 300 to about 500 μm.

9. The method of claim 1, wherein the ratio of liquid to particles is from about 0.75 to about 0.85.

10. A method of making a fused bioresorbable sponge suitable for use as a carrier for osteogenic protein, said method comprising:

a) preparing particles of a porous particulate polymer comprising lactic acid and glycolic acid;

b) placing the particles in a container together with liquid containing ethanol and a surfactant, such that the ratio of liquid to particles in the mixture is from about 0.70 to about 0.90 (volume/volume);

c) heating the container containing the particles and liquid for a period of time from about 1 to about 60 minutes at a temperature of about 60° C.;

d) optionally cooling the container for a period of about 5 minutes or more at a temperature of about 4° C.; and e) removing the particles and liquid in the form of a fused bioresorbable sponge from the container.

11. A fused bioresorbable sponge of porous particulate polymer made of a material selected from the group comprised of polylactic acid, polyglactic acid, and. Copolymers of lactic acid and glycolic acid, made by the method of claim 1.

12. A composition comprising a fused bioresorbable sponge according to claim 11 and an osteogenic protein.

* * * * *

UNITED STATES PATENT AND TRADEMARK OFFICE
CERTIFICATE OF CORRECTION

PATENT NO. : 5,520,923
DATED : May 28, 1996
INVENTOR(S) : Tjia et al.

It is certified that error appears in the above-indentified patent and that said Letters Patent is hereby corrected as shown below:

At column 1, line 46, please change "carder" to --carrier--

At column 1, line 59, please change "COPLA" to --("OPLA")--

At column 1, line 66, please change "Clin, Orthop." to --Clin. Orthop.--

At column 2, line 2, please change "Plaster of Partis" to --Plaster of Paris--

At column 2, line 49, please change "fig" to --(Tg)--

At column 10, line 51, please change "tum particles" to --µm particles--

At column 10, line 55, please change "500-710 uparticles" to --500-710 µm particles--

UNITED STATES PATENT AND TRADEMARK OFFICE
CERTIFICATE OF CORRECTION

PATENT NO. : 5,520,923     Page 2 of 2
DATED      : May 28, 1996
INVENTOR(S): Tjia et al.

It is certified that error appears in the above-indentified patent and that said Letters Patent is hereby corrected as shown below:

At column 12, line 13, please change "Particels" to --Particles--

At column 14, line 3, please change "polyglactic acid, and. Copolymers" to --polyglactic acid, and copolymers--

Signed and Sealed this

Nineteenth Day of November, 1996

*Attest:*

BRUCE LEHMAN

*Attesting Officer*     *Commissioner of Patents and Trademarks*